(12) United States Patent
Jensen

(10) Patent No.: US 7,341,972 B2
(45) Date of Patent: Mar. 11, 2008

(54) SINGLET OXYGEN CATALYSTS INCLUDING CONDENSED CARBON MOLECULES

(76) Inventor: Anton W. Jensen, 516 W. Grand Ave., Mt. Pleasant, MI (US) 48858

( * ) Notice: Subject to any disclaimer, the term of this patent is extended or adjusted under 35 U.S.C. 154(b) by 294 days.

(21) Appl. No.: 10/967,823

(22) Filed: Oct. 18, 2004

(65) Prior Publication Data

US 2005/0059845 A1 Mar. 17, 2005

Related U.S. Application Data

(63) Continuation-in-part of application No. 10/126,308, filed on Apr. 19, 2002, now Pat. No. 6,806,223.

(51) Int. Cl.
*B01J 27/24* (2006.01)
(52) U.S. Cl. ............. 502/200; 502/150; 502/159; 502/167; 502/172; 502/527.24; 562/418; 562/421; 562/462
(58) Field of Classification Search ............. 562/418, 562/421, 462; 502/150, 159, 167, 172
See application file for complete search history.

(56) References Cited

U.S. PATENT DOCUMENTS

| | | | |
|---|---|---|---|
| 4,315,998 A | 2/1982 | Neckers et al. | |
| 5,041,516 A * | 8/1991 | Frechet et al. | ............... 528/44 |
| 5,153,166 A | 10/1992 | Jain et al. | |
| 5,294,732 A | 3/1994 | Chiang et al. | |
| 5,308,481 A | 5/1994 | Stalling et al. | |
| 5,367,051 A | 11/1994 | Narang et al. | |
| 5,382,718 A | 1/1995 | Bekiarian et al. | |
| 5,386,048 A | 1/1995 | West et al. | |
| 5,530,092 A * | 6/1996 | Meijer et al. | ............... 528/363 |
| 5,886,110 A * | 3/1999 | Gozzini et al. | ............. 525/472 |
| 5,904,852 A | 5/1999 | Tour et al. | |
| 5,981,684 A * | 11/1999 | Bruchmann et al. | ............ 528/45 |
| 6,103,848 A * | 8/2000 | Decker et al. | ................ 528/21 |
| 6,162,926 A | 12/2000 | Murphy et al. | |
| 6,162,936 A * | 12/2000 | Alt et al. | ...................... 556/43 |
| 6,319,674 B1 | 11/2001 | Fulcrand et al. | |
| 6,359,061 B1 | 3/2002 | Swayze et al. | |
| 6,362,011 B1 | 3/2002 | Massey et al. | |
| 6,380,266 B1 | 4/2002 | Katz et al. | |
| 6,448,412 B1 | 9/2002 | Murphy et al. | |
| 6,803,106 B2 * | 10/2004 | Campbell et al. | ........... 428/403 |
| 6,806,223 B2 * | 10/2004 | Jensen | ....................... 502/150 |

OTHER PUBLICATIONS

Latassa et al., "Polysiloxane supported fullerene derivative as a new heterogeneous sensitser for the selective photooxidation ofg sulfiides to sulfoxides by 1O2", Journal of Materials Chemistry, Feb. 28, 2002.*

Daniel Latassa, Olivier Enger, Carlo Thilgen, Tilo Habicher, Heribert Offermans, Francois Diederich, "Polysiloxane-supported fullerence derivative as a new heterogeneous sensitiser for the selective photooxidation of sulfides to sulfoxides by 1O2". Journal of Materials Chemistry, 2002, vol. 12, pp. 1993-1995.

* cited by examiner

*Primary Examiner*—David M Brunsman
(74) *Attorney, Agent, or Firm*—Harness, Dickey & Pierce, P.L.C.

(57) ABSTRACT

The present invention relates to novel singlet oxygen catalysts useful for the production of specialty chemicals. The catalysts include a core material selected from amine coated polymeric beads, amine coated glass beads and multi-generational dendrimers to which condensed carbon molecules are bonded. These catalysts may in turn give rise to other solid phase heterogeneous catalysts useful for stereoselective or regioselective reactions, by way of non-limiting example.

11 Claims, 14 Drawing Sheets

SINGLET OXYGEN CATALYSTS INCLUDING CONDENSED CARBON MOLECULES

This application is a continuation-in-part of U.S. patent application Ser. No. 10/126,308 filed Apr. 19, 2002, now U.S. Pat. No. 6,806,223. The disclosure of the above application is incorporated herein by reference.

Work on this invention may be sponsored in part by the National Science Foundation, Application No. 0213385. The Government may have certain rights to the invention.

FIELD OF THE INVENTION

The present invention relates to singlet oxygen catalysts including core materials coated with condensed carbon molecules such as fullerenes and the use of these materials for the production of specialty chemicals.

BACKGROUND OF THE INVENTION

Polymer beads coated with dyes such as Rose Bengal have been made and used to photo-catalyze reactions in organic solvents as described in U.S. Pat. No. 4,315,998 to Neckers et al. While the dye coated molecules described appear to be effective for certain photo-catalyzing reactions in solvents, these dyed molecules do not have the convenient functionality for covalently bonding other molecules. As such, dye coated polymer beads cannot be effectively modified to perform stereoselective $^1O_2$ oxidations as set forth in accordance with the teachings of the present invention. Further, fullerenes have both excellent stability and a high quantum efficiency for $^1O_2$ formation, which makes fullerene coated catalysts very stable.

Certain other catalysts have been reported as being capable of photo-catalytic reactions in water. According to an article appearing in the J. Am. Chem. Soc., Vol. 101, pgs. 4016-4017 authored by A. P. Schapp et al., a more hydrophilic bead was made by copolymerization of 3-cholomethylstryene, 4-cholomethylstryene, ethylene glycol dimethacrylate and ethylene glycol monomethacrylate. Rose Bengal was then attached to this bead and shown to form $^1O_2$ in water.

Still another aqueous photo-catalyst was described in an article by F. Prat et al. appearing in Photochemical Photobiol., Vol. 67, pgs. 626-627. According to this article, a bead linked to an amino group by a long poly(ethylene glycol) chain was functionalized with Rose Bengal and used to form $^1O_2$ in water.

While the above mentioned photo-catalysts appear useful, the aqueous catalysts tend to be difficult to make or do not have convenient functionality at the outermost layer necessary for covalently bonding other molecules.

More recently, polymeric beads have been demonstrated as being coatable with fullerenes and fullerene derivatives as described in U.S. Pat. No. 5,308,481. According to this patent, a fullerene derivative was made according to a three step process involving reduction of the fullerene, addition of bromine to a double bond and replacement of one of the fullerene bromines with 8-bromo-1-octanol. This derivative was then added to an amine coated polymer bead by displacement of a tethered bromine. While this method does involve addition of an amine to a derivatized fullerene, the process involves three additional steps, none of which are trivial. The process described in the present invention represents a significant improvement on the mode of attaching fullerenes to beads. Other attachment modes are also briefly described at the end of the '481 patent described in accordance with the teachings of the present invention.

Research has additionally shown that fullerenes placed on films can be used to photochemically form singlet oxygen. However, films lack sufficient surface area to be able to make enough $^1O_2$ for the materials to be used effectively as catalyst materials.

Singlet oxygen is commonly used as an oxidizing agent in organic synthesis and is an essential component in the production of photo-dynamic therapy for the treatment of cancer.

SUMMARY OF THE INVENTION

The need for catalysts which can be used to produce complex chemical compounds in an environmentally friendly way are in great demand. For example, pharmaceutical companies spend billions of dollars annually preparing drugs as the demand for new drugs continues to rise. However, it is well recognized that pharmaceutical companies are required to spend enormous funds on research and development just to get a drug to market. Thus, there is an ever increasing need for low cost, effective drug precursors which can help reduce research costs and ultimately lower a drug's costs.

According to the teachings of the present invention, certain core materials can be coated with condensed carbon molecules such as fullerenes having available functional groups for covalently adding hydrophilic components, thus allowing singlet oxygen $^1O_2$ reactions to be carried out in water or selective solvents. In particular, derivatized or underivatized condensed carbon molecules can be utilized to coat polymeric resin beads, glass beads or dendrimers to form catalysts and precursor components for stereoselective or regioselective reactions, by way of non-limiting example. By the phrase "condensed carbon molecules" it is meant that a variety of normally hollow carbon molecules such as fullerenes (namely $C_{32}$, $C_{60}$, $C_{70}$ and $C_{84}$) and carbon nanotubes which have a high quantum efficiency for the formation of singlet oxygen may be employed.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

The present invention relates in part to catalytic products in the form of core materials comprising polymer resin beads or multi-generational dendrimers having condensed carbon molecules such as fullerenes or carbon nanotubules attached. These core materials, which are generally effective in solvents such as chloroform to form singlet oxygen, $^1O_2$ from $O_2$ when exposed to light, may in turn be provided with hydrophilic groups, thereby forming catalysts useful in water or selective solvents as will be described in greater detail below.

Figure 1:
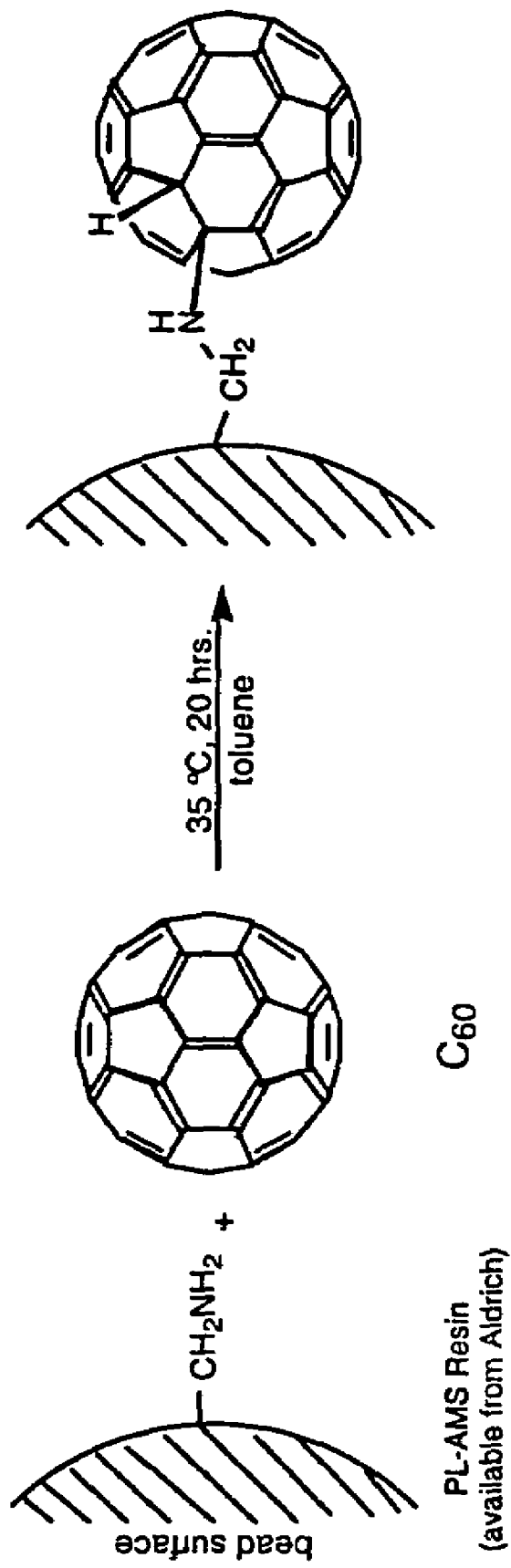
FIG. 1 illustrates a reaction mechanism for forming a first core material (catalyst I)

Referring to FIG. 1, a first core material is shown being formed employing amine coated beads such as amine coated polymeric beads which are commercially available from Aldrich Chemical under the trade name PL-AMS or amine coated glass beads which are available from Sigma-Aldrich. In addition to amine coated polymeric or glass beads, dendrimers could be attached to polymeric beads or glass beads in addition to or in lieu of amine groups as noted above. According to the present invention, catalytic precursors or core materials can be formed by reacting with an excess of underivatized fullerene molecules with amine or dendrimer coated beads slightly above ambient temperature in a solution of toluene with stirring for about two hours. The solution tends to lose some of the purple fullerene color as the beads are coated, thus indicating that the reaction is nearing completion. However, by stirring for an extended period of time, a complete reaction can be assured.

The core materials are then preferably rinsed with warm toluene or various other solvents, followed by soxhlet extraction for 20 hours with methylene chloride essentially leaving only the core material coated with the condensed carbon molecules (catalyst I).

Figure 2:
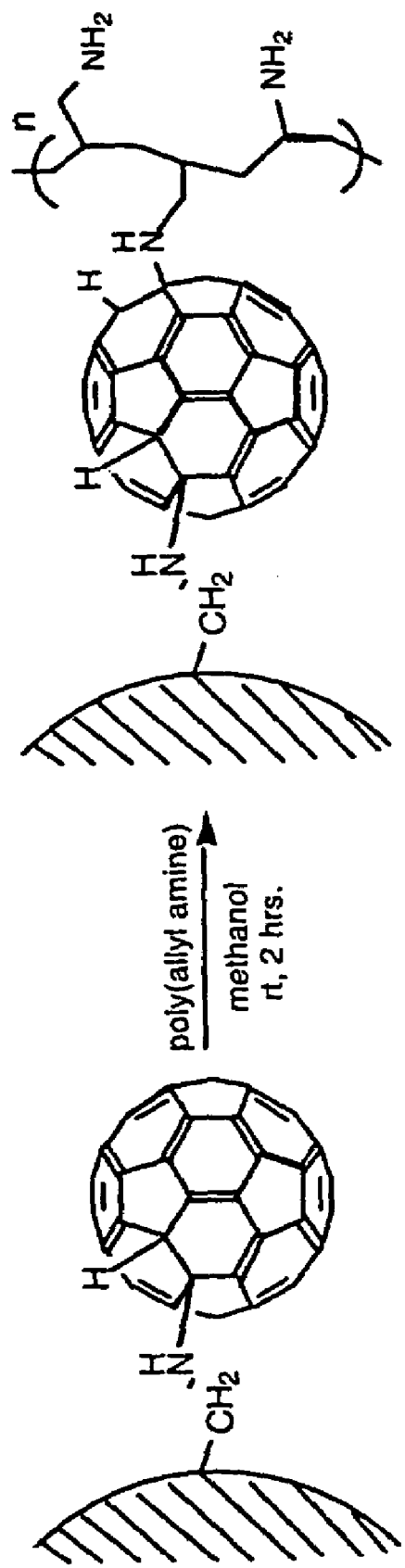
FIG. 2 illustrates a reaction mechanism demonstrating the addition of hydrophilic groups to the core material of FIG. 1 (catalyst II)

A second core material according to the teachings of the present invention as depicted in FIG. 2 can be formed by introducing the first core material as described above to a methanolic solution of poly(allyl amine) for approximately two hours, with stirring (catalyst II).

Figure 3:
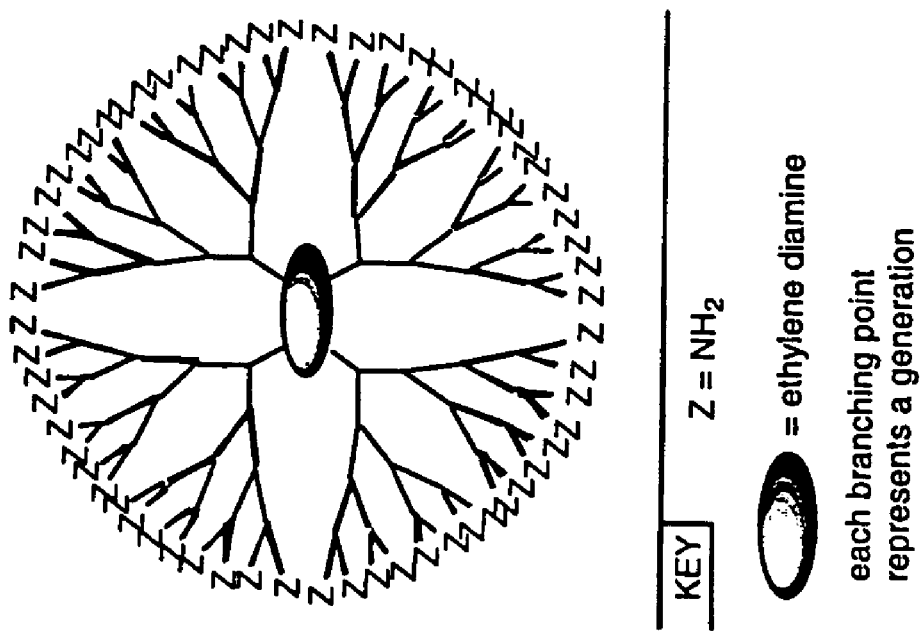
FIG. 3 illustrates a multi-generational dendrimer that can be used in association with condensed carbon molecules to form alternative core materials.

Still another core material as depicted in FIG. 3 can be made by utilizing multi-generational dendrimers wherein each branching point represents a new generation. Since multi-generational dendrimers tend to be smaller than polymeric or glass beads, dendritic cores would provide a greater surface area for the attachment or condensed carbon molecule groups.

Upon forming the core materials, various reactions can be carried out to test the catalytic ability of the core materials as set forth in FIG. 4a-4d. In particular, referring to FIG. 4a, an ene reaction can be carried out by adding the ene substrate to an organic solvent containing catalyst I and bubbling air through the sample while irradiating with light.

Figure 4:
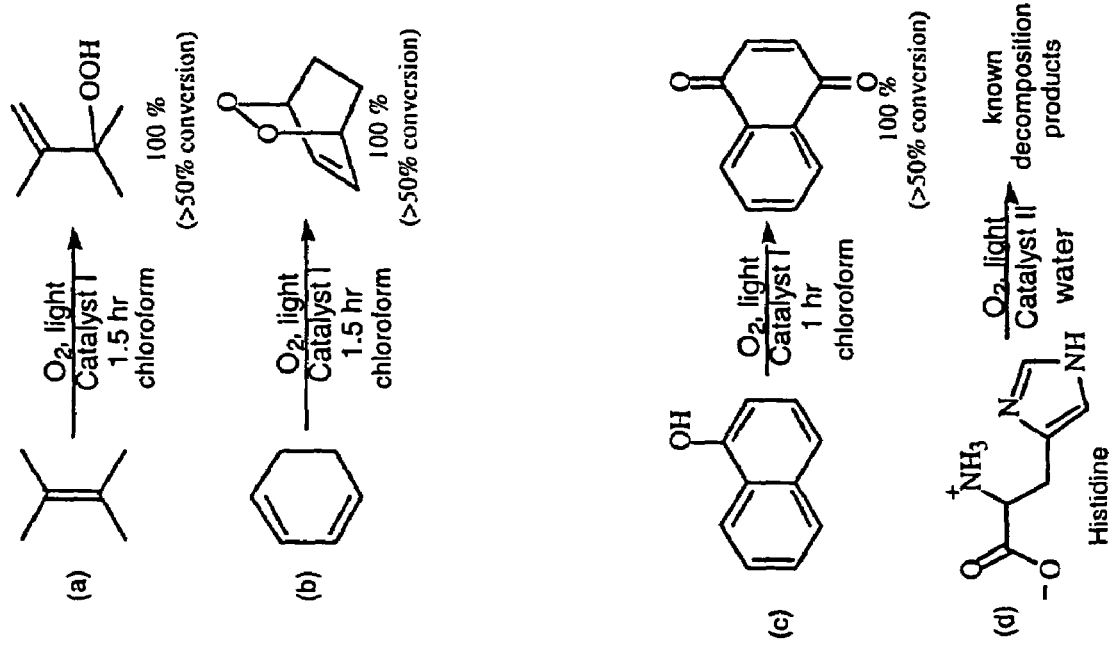
FIG. 4a)-4d) illustrates a series of reactions employing the first or second core materials of FIGS. 1 and 2, respectively.

Referring to FIG. 4b, a Diels-Alder reaction can be carried out by introducing the Diels-Alder substrate to an organic solvent containing catalyst I and bubbling air through the sample while irradiating with light.

Referring to FIG. 4c, phenols can be oxidized to quinones by placing the phenol in an organic solvent containing catalyst I and bubbling air through the sample while irradiating with light.

Referring to FIG. 4d, still another reaction is illustrated which exhibits that the second core material can be utilized in an aqueous solution, namely, water. According to the reaction of FIG. 4d, histidine is photo-decomposed to various products by placing it in water containing catalyst II and bubbling air through the sample while irradiating with light.

Figure 5:
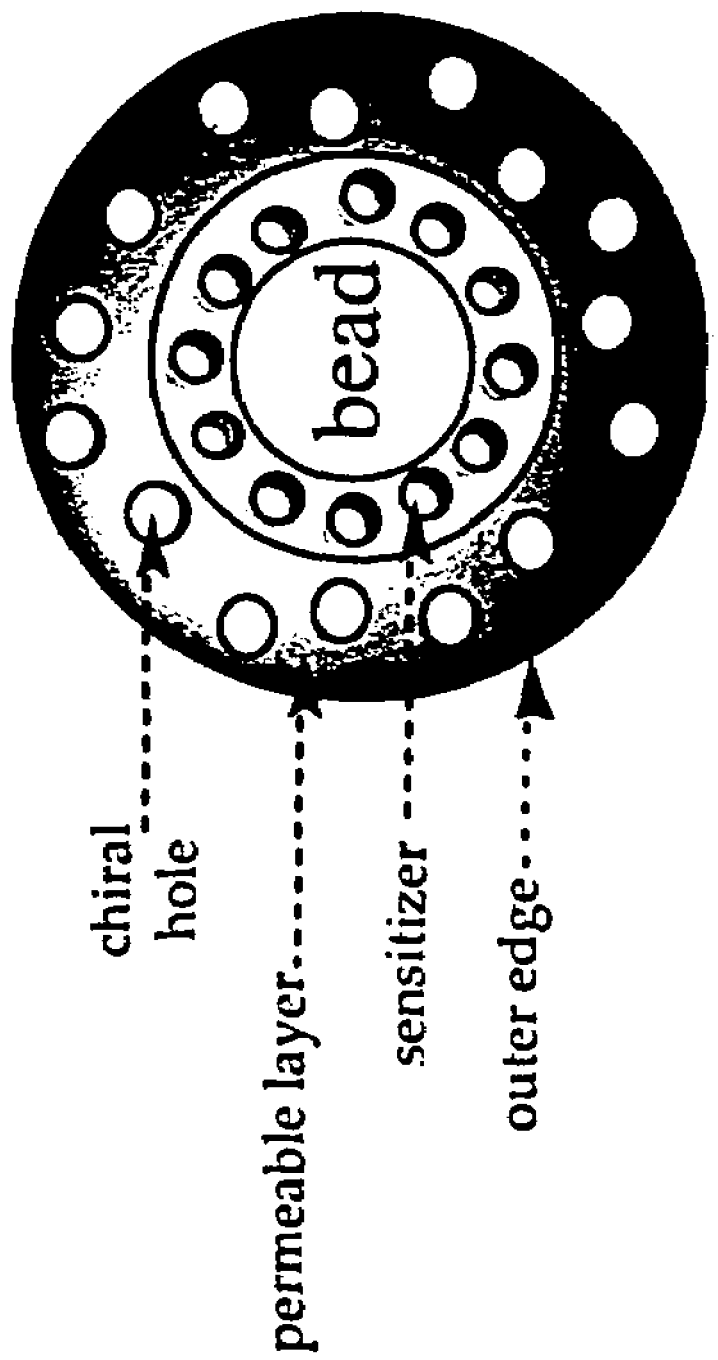
FIG. 5 is a cross sectional schematic view illustrating the core material of FIG. 1.
Figure 6:
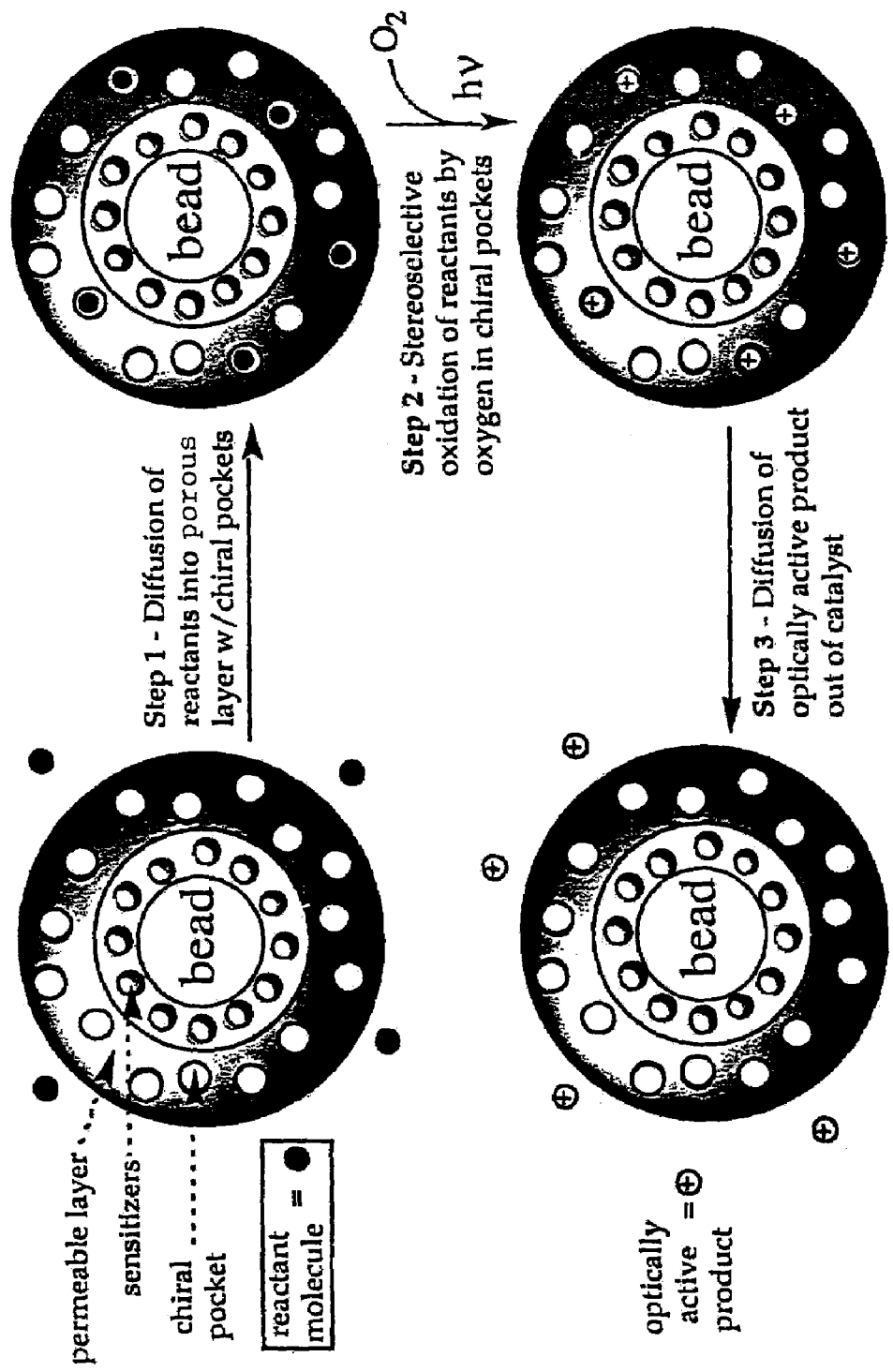
FIG. 6 is a cross sectional schematic view illustrating the sequential production of a specialty chemical compound employing the core material of FIG. 5.

In addition to clearly having the ability to photo-catalyze various singlet oxygen reactions as demonstrated above, the core materials can be modified to include an outer portion containing chiral spaces to form solid phase heterogeneous catalytic products capable of stereoselective or regioselective reactions by way of non-limiting example. As illustrated in FIGS. 5 and 6, this objective can be accomplished by layering core materials with chiral pockets (analogous to enzyme active sites).

In this regard, the solid phase heterogeneous catalytic products for carrying out stereoselective or regioselective reactions can be thought of as consisting of two distinct parts. The first part, hereinafter referred to as the "core material" consists of a substantially spherical support, i.e., a polymeric bead, glass bead or multi-generational dendrimer, surrounded by a sensitizing layer, i.e., the condensed carbon molecules as described above. The second part of the solid phase heterogeneous catalytic product includes an "outer portion" which is at least semi-permeable. This outer portion can be in the form of layered polyelectrolyte films (LPFs) and hyperbranched polymer films (HPFs), by way of non-limiting example. In order to avoid oxidation from occurring outside of the catalytic product, the material used to make the outer portion must be thick enough to prevent singlet oxygen from escaping beyond the outer portion. Thus, the outer portion should essentially be a layered component, preferably a multi-layered component, having an overall thickness in the range of between about 200 to about 500 angstroms.

Chiral pockets as the term is used herein can be formed into the catalytic products' outer portion via polyelectrolytes. Theoretically, either the backbone or pendent groups of the polyelectrolyte could be chiral. Alternatively, the core can be covered with achiral materials that are subsequently reacted with a chiral reagent that binds to the outer layers, thereby making them chiral.

To form solid phase heterogeneous catalytic products employing polyelectrolyte films or LPFs, a core material is immersed in a polymeric solution including ionizable groups, e.g., either a polycation or polyanion. Useful polycation solutions may include, by way of non-limiting example, poly(sulfoniums), poly(phosphoniums), poly(ammoniums) and, preferably, poly(allyl ammonium chloride).

Useful polyanion solutions may include poly(acrylates), poly(aspartates), poly(sulfonates), poly(phosphates) and poly(phenoxides). As should be clear, various polymers with an ionizable group may be used.

Figure 7:
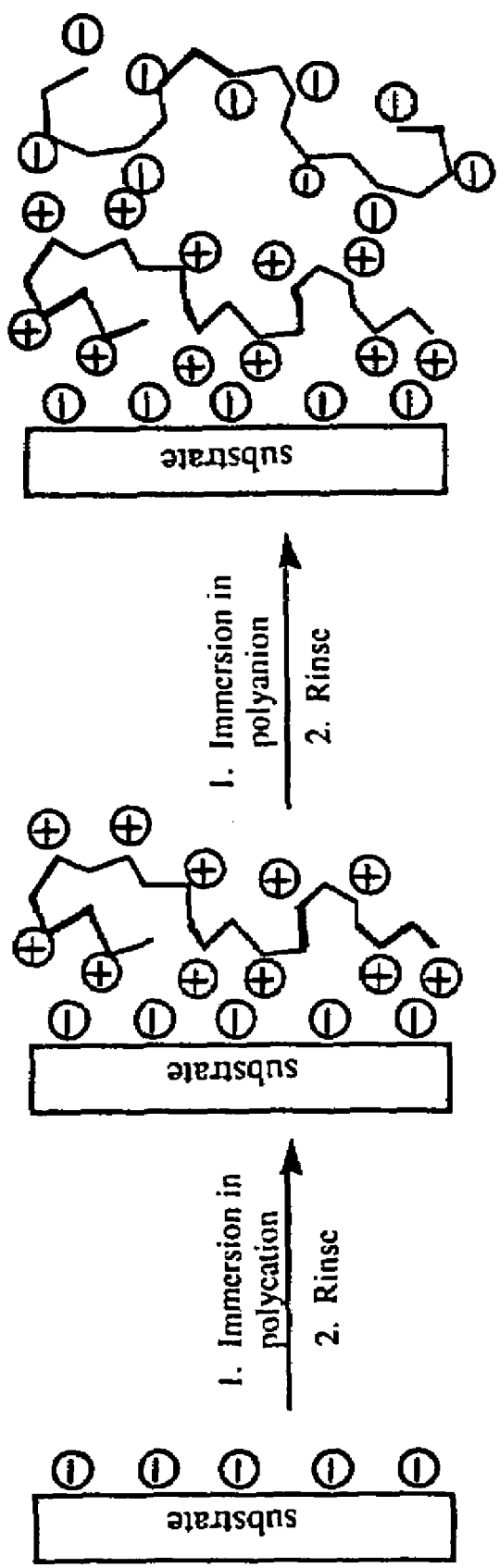
FIG. 7 illustrates a reaction mechanism for the assembly of polyelectrolyte films to be added to the core material to form a catalytic component.

Upon adding the first layer, the first layer is then rinsed with water prior to immersion in a complimentary polyion that electrostatically binds to the first layer as demonstrated in FIG. 7. Utilizing sequential alternate polyelectrolyte deposition techniques, preferably rinsing each layer, a multilayered LPF can be formed. Polyelectrolyte layers may be added to catalyst cores according to FIG. 8. Thus, the film permeability and thickness can be adjusted by varying the number of layers added and the polyelectrolyte solutions employed. Also, the polarity of the layers being constructed can be controlled to influence the migration rate of $^1O_2$ through the layers. Additionally, the terminal or outer layers can be capped or derivatized to include hydrophilic groups, for example. Still another option is to employ $^1O_2$ quenchers such as nickel chelates to block $^1O_2$ transport. If desired, the layers may be cross linked to increase thermal stability.

Figure 9:
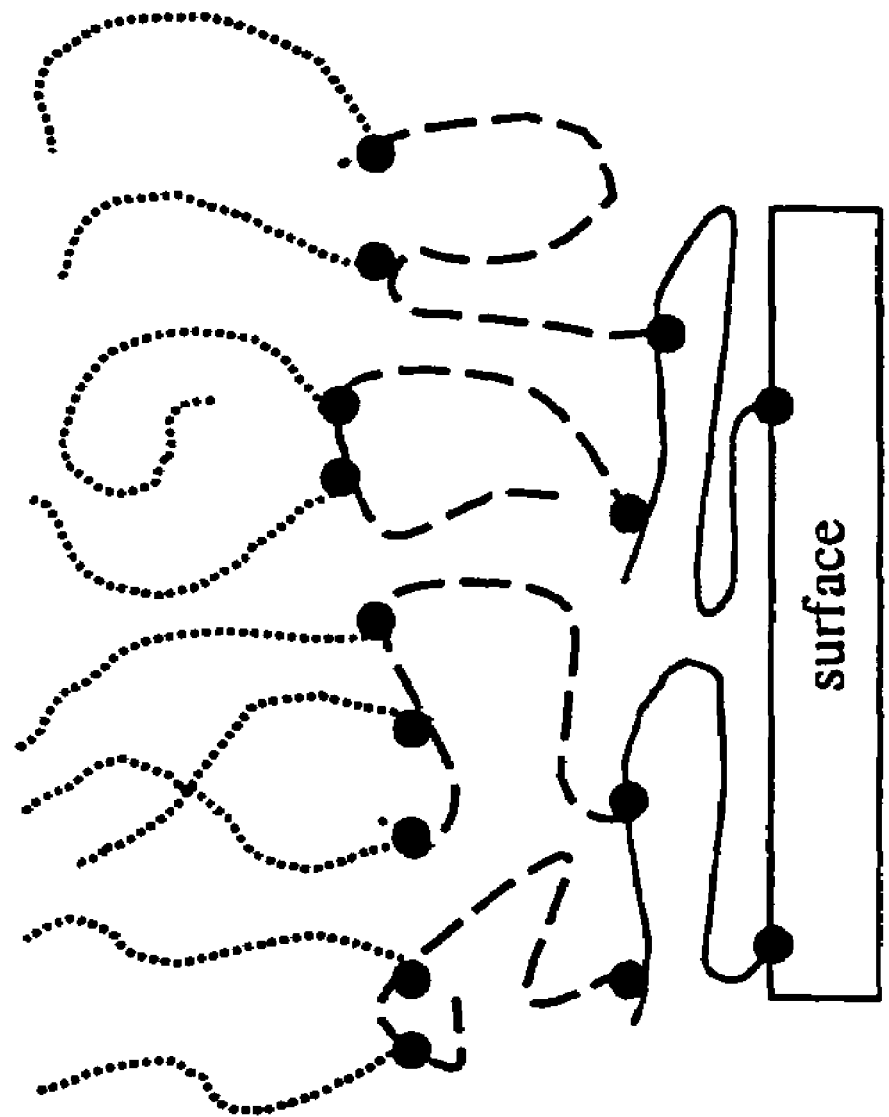
FIG. 9 illustrates the architecture of hyperbranched films to be added to the core material to form a catalytic component.

A method of preparing solid phase heterogeneous catalysts including hyperbranched polymer films or HPF's will now be described. Hyperbranched polymer films or HPFs consist of polymer chains joined together by connecting the ends of certain polymer chains (i.e., generation II) to activated functional groups tethered off the backbone of previously layered polymers (i.e., generation I) as exhibited in FIG. 9.

Figure 8:
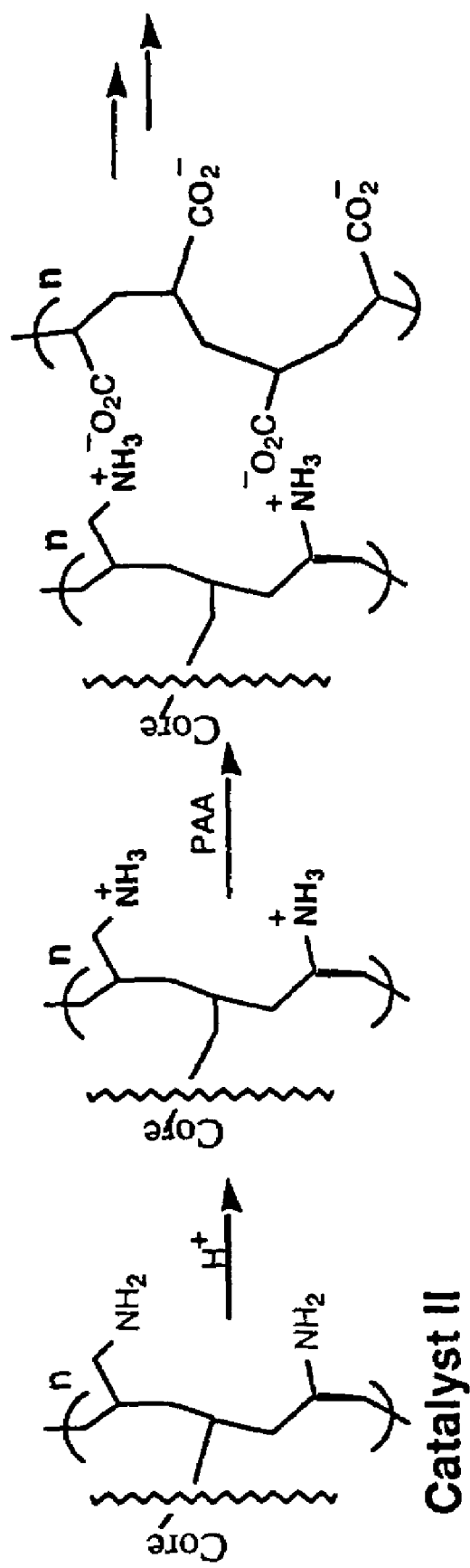
FIG. 8 illustrates a reaction mechanism for the formation of multi-layered polyelectrolyte films to be added to the core material to form a catalytic component.
Figure 10:
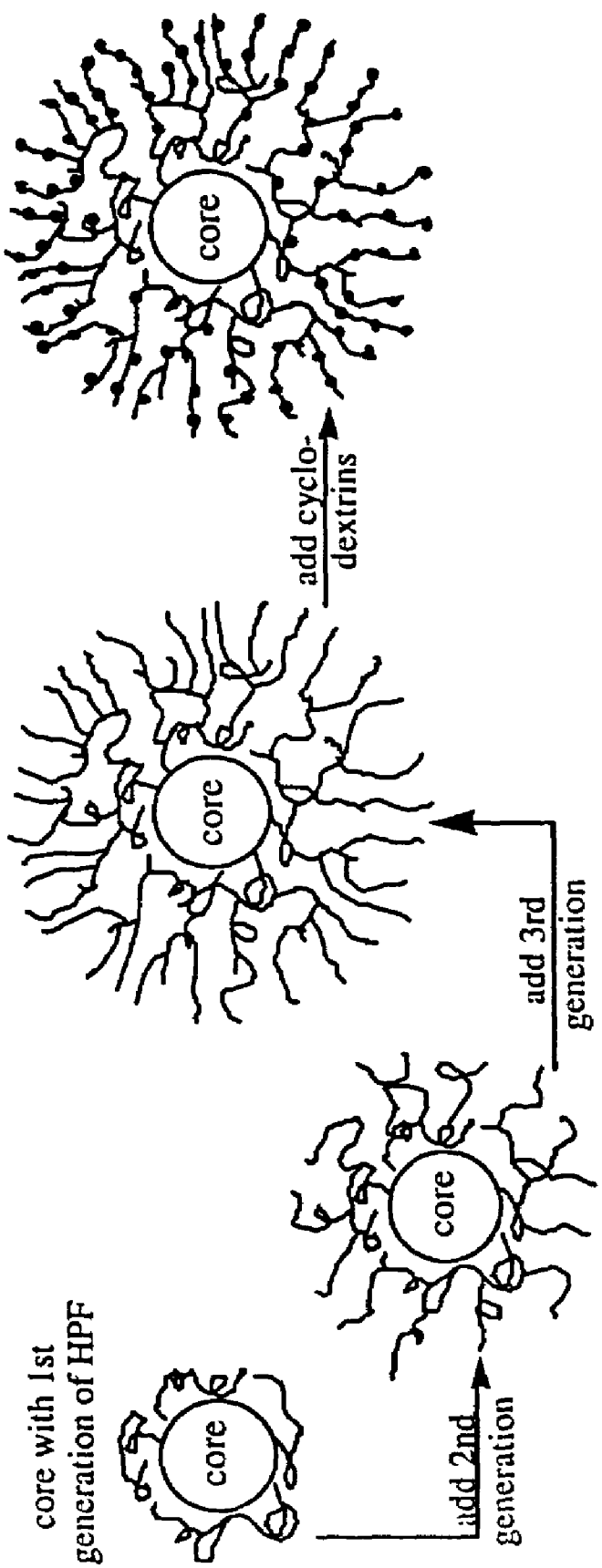
FIG. 10 illustrates the sequential addition of activated acid groups and β-cyclodextrins to form hyperbranched catalytic components.

A preferred core material useful in forming solid phase heterogeneous catalytic products are the above referenced materials which include an acid modified outer surface as represented in FIG. 8. This acid coated core material is immersed in a solution of ethyl chloroformate to activate the acid groups. Thereafter, the activated acids are reacted with amino terminated poly(tert-butyl acrylate) to give rise to the first generation of material, represented by the solid lines of FIG. 9. Thereafter, the tert-butyl groups are hydrolyzed by introducing the material into para-toluene sulfonic acid (pTsOH) to form acid groups all along the polymer. By repeating this sequence of steps, i.e., acid activation, reaction with a tert-butyl polymer and hydrolyzing the tert-butyl groups, a catalytic HPF material containing numerous generations of acid groups can be formed as shwon in FIG. 10.

Figure 11:
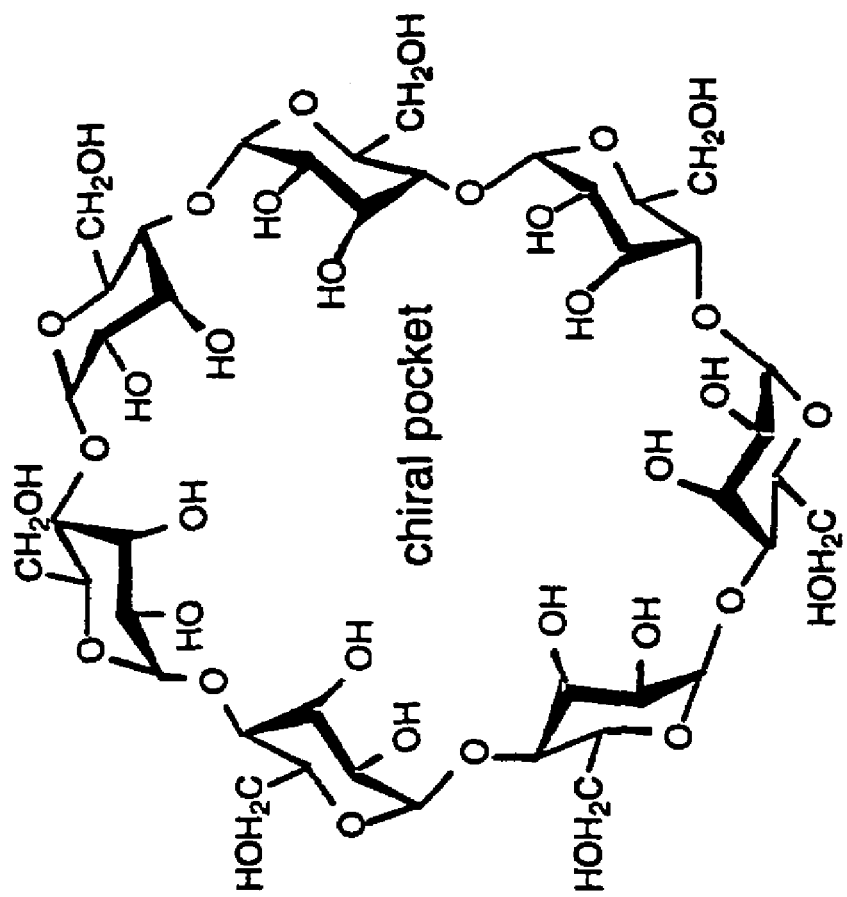
FIG. 11 is a schematic view illustrating a cyclodextrin molecule having a chiral pocket.
Figure 12:
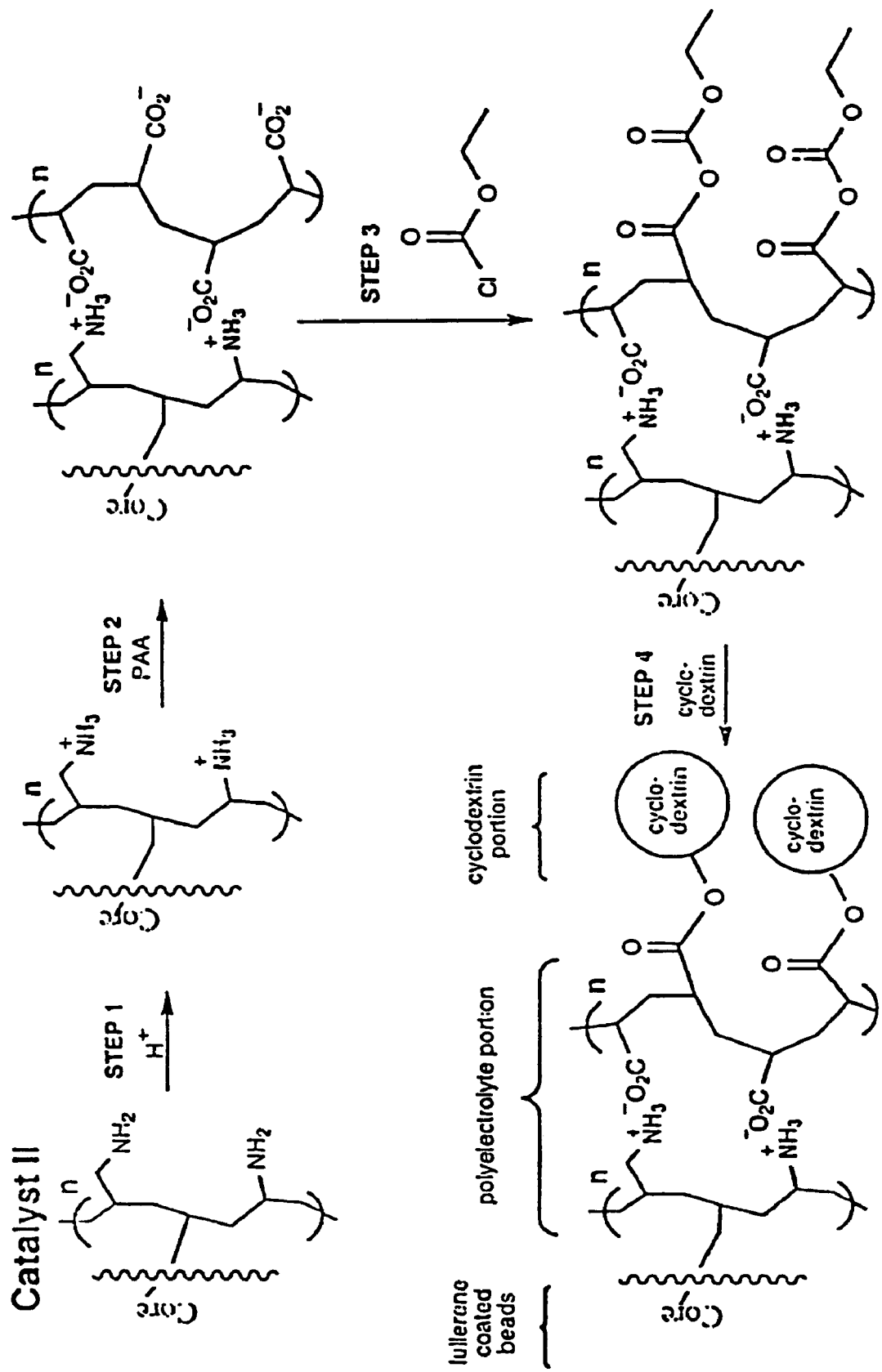
FIG. 12 illustrates the sequential reaction mechanism for forming a catalytic product capable of stereoselective or regioselective reactions.

Once the catalytic HPF material containing the desired number of acid groups is formed, the material is introduced into solutions of ethyl chloroformate and then β-cyclodextrin whereby the alcohol groups of the cyclodextrin form ester linkages with the numerous acid groups as demonstrated in FIG. 12. As should be understood by one skilled in the art, cyclodextrins are cyclic sugar molecules including a chiral cavity or "pocket" as illustrated in FIG. 11.

Figure 13:
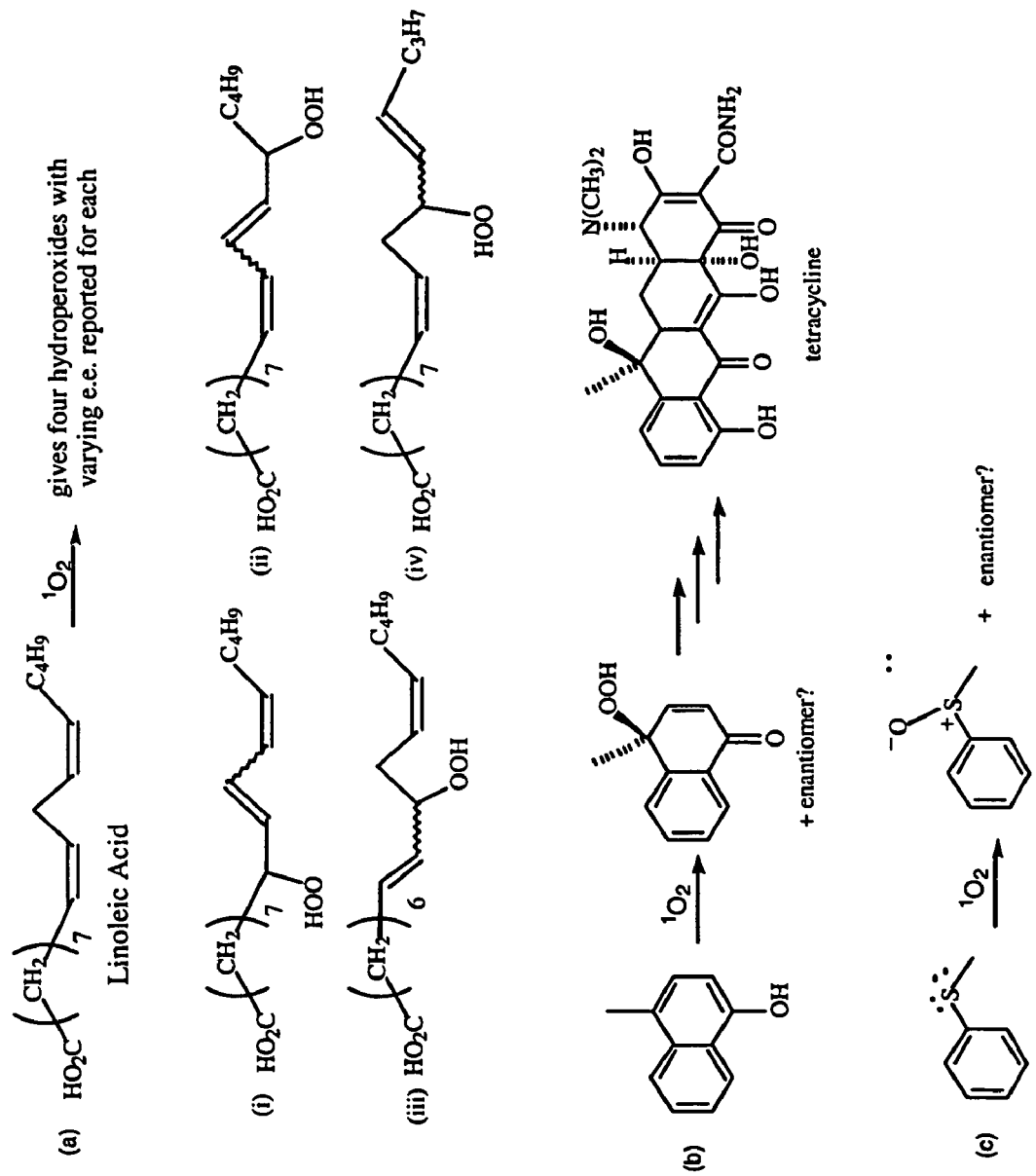
FIG. 13 illustrates three classes of theoretical stereoselective reactions utilizing the catalytic product of FIG. 12.

Referring to FIG. 13, two theoretical classes of theoretical stereoselective reactions and one class of reaction in which stereoselectivity has been achieved are illustrated. In particular, according to FIG. 13a, by introducing linoleic acid within the chiral pockets of the cyclodextrin, (represented as the reactant molecule in FIG. 6), it is expected that at least four different hydroperoxide molecules with varying emantiomeric excess can be obtained. As demonstrated by (b) in FIG. 13, another theoretical stereoselective reaction involves the endoperoxidation of napthol giving an intermediate which should be useful in the synthesis of tetracycline. As demonstrated in FIG. 13(c), a reaction involving the production of sulfoxides in which stereoselective singlet oxygenation has been achieved is illustrated. To evaluate the commercial viability, the enantiomeric excess of such stereoselective reactions can be measured using HPLCs equipped with chiral columns as is known in the art.

As should be understood by those skilled in the art, catalysis can be influenced by a number of factors. For example, the reaction mixture could be continuously exposed to light while the catalysts are suspended in a solvent. Under these conditions, oxygen would continually diffuse through the permeable layer of the catalyst to the sensitizer layer, where it would be converted to $^1O_2$ (because $O_2$ is small, it will diffuse throughout the catalyst). The $^1O_2$ would then diffuse in all directions, including towards the outermost layer. As long as the permeable layer is thick enough, $^1O_2$ will not escape the outer edge of the permeable layer until it decays back to $^3O_2$ (which is unreactive ground state oxygen). As the $^1O_2$ is generated, organic reactants diffuse into and out of the permeable layer and dock in the chiral pockets as shown in FIG. 6, provided there is favorable binding to those pockets. Stereoselective reactions will occur when $^1O_2$ encounters a docked organic reactant.

Another way the catalyst could operate would be to allow the organic reactant to be absorbed into the catalysts by suspending the catalyst in a liquid solution of reactant, followed by removal of the liquid phase solvent. As long as interactions with the chiral pockets are favorable, most reactants would then be docked in the dry catalyst. The catalysts could then be exposed to oxygen gas and light.

Figure 14:
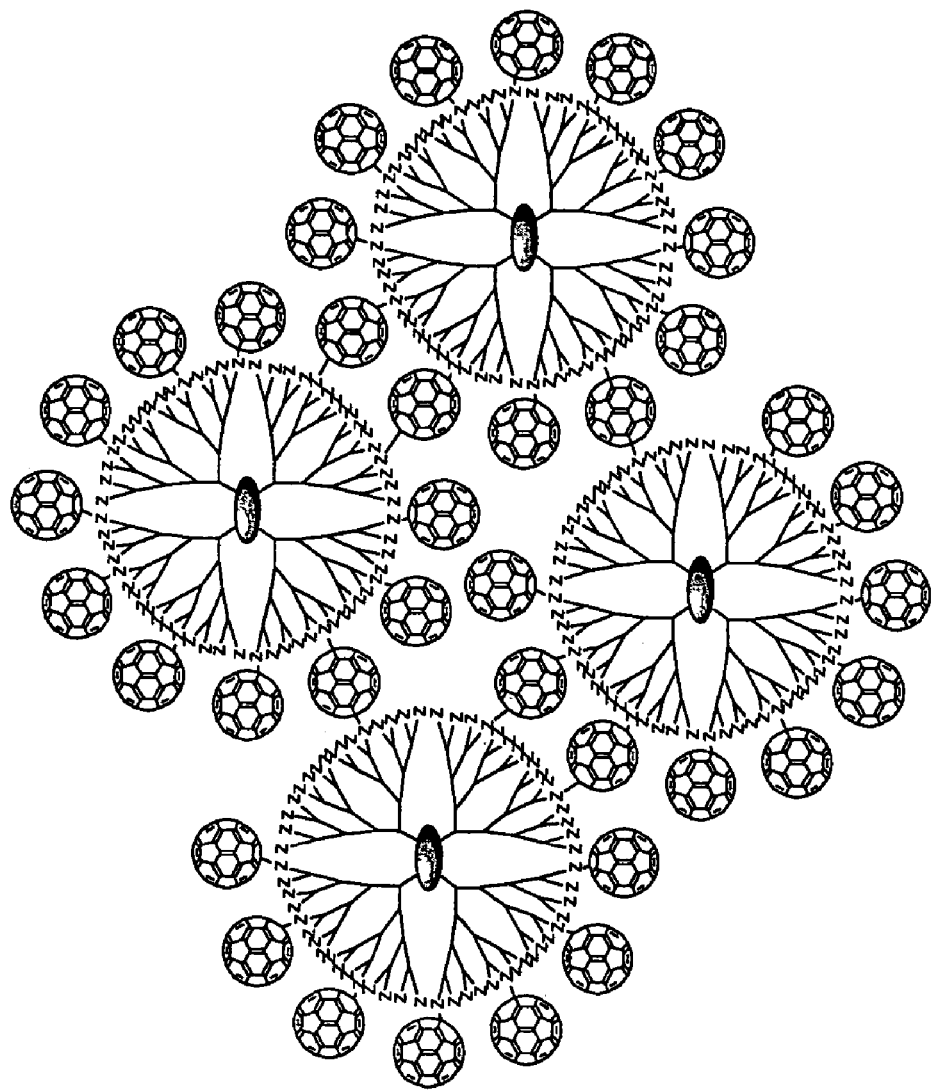
FIG. 14 is a theoretical depiction of a dedrimer catalyst molecule.

Referring to FIG. 14 a condensed carbon dendrimer catalyst molecule is depicted which results from the method now described. Initially, condensed carbon molecules, such as fullerene by way of non-limiting example, are dissolved in solvent and a predetermined amount of dendrimer such as PAMAM by way of non-limiting example is dissolved in a separate volume of solvent. Once the condensed carbon molecules and dendrimer are dissolved, the dendrimer solution is mixed with the condensed carbon molecule solution until a color change occurs indicating a reaction between the condensed color molecules and dendrimers. Upon reaction, the solvent is removed to leave a raw condensed carbon molecule, dendrimer catalyst. The raw catalyst is then extracted with a solvent other than that used in the initial reaction. Finally, the extracted raw condensed carbon dendrimer catalyst is purified in a stepwise chromatographic reaction where the extracted raw catalyst is passed through a chromatograph containing a solvent suitable for removing unreacted condensed carbon molecules. Thereafter, the catalyst is passed through a chromatograph containing a solvent suitable for collecting a purified condensed carbon dendrimer catalyst.

A detailed example of the preparation of a condensed carbon dendrimer catalyst in accordance with the teachings of the present invention will now be provided.

EXAMPLE I

1. Weigh 401.2 mg of $C_{60}$ and dissolve in 700 mL of pyridine.
2. Weigh 42 mg of G4 PAMAM dendrimer and disperse in 200 mL of pyridine solution.
3. Allow both the solutions to stir overnight. After overnight stirring the $C_{60}$ solution is a bright purple color and G4 dendrimer is finely dispersed in pyridine.
4. Add the dendrimer pyridine solution dropwise to the $C_{60}$-pyridine solution. A small amount of precipitate begins to form. Continue to add dendrimer solution and allow the solution to stir overnight. The $C_{60}$-dendrimer solution takes on a dark brown color.

5. Remove pyridine by distillation under high vacuum. A brownish black crude $C_{60}$-dendrimer residue is obtained.
6. Extract the residue with benzene.
7. Distill off benzene to obtain unpurified $C_{60}$-dendrimer catalyst.
8. Run column chromatography on catalyst first by using toluene (which removes unreacted $C_{60}$) and then with pyridine to collect $C_{60}$-dendrimer catalyst.

Upon preparation of the above example, mass spectal and thermal gravimetric analysis were conducted on the sample. The results indicate that the catalytic molecule includes approximately four PAMAM dendrimers for every eighty $C_{60}$ fullerenes. As such, a theoretical depiction of the resultant molecule is provided in FIG. 14.

Some of the advantages of the catalysts described herein are that 1) singlet oxygen may be used to carry out several different types of oxidation reactions; 2) performing these reactions stereoselectively could lead to new methods for making valuable chiral compounds; 3) these catalysts combine two valuable features of other $^1O_2$ catalysts in that they offer the handling ease of heterogeneous catalysis and the synthetic utility of stereoselective catalysis; 4) the core materials are easy to form from commercially available materials; and 5) these catalyzed reactions are environmentally friendly because they involve light, oxygen and a reusable catalyst.

Among the many proposed uses for the solid phase heterogeneous catalytic products of the present invention are 1) to be used in the synthesis of various organic compounds, including stereo- and regio-selective reactions as discussed above; 2) to be used to generate $^1O_2$ in the presence of cancer cells, thereby killing them; and 3) to be used to clean water that has been contaminated by various biological specimens that do not survive exposure to $^1O_2$.

The description of the invention is merely exemplary in nature and, thus, variations that do not depart from the general scope of the invention are intended to be included.

What is claimed is:

1. A method of carrying out stereoselective or regioselective chiral reactions, said method comprising the steps of:
    a) providing a catalytic product including a core material having amine groups and condensed carbon molecules selected from the group consisting of fullerenes and carbon nanotubes bonded directly to said amine groups and an outer portion bonded to said condensed carbon molecules including chiral pocket pockets;
    b) introducing reactant molecules into the chiral pockets of said catalytic product; and
    c) activating the selective oxidation of said reactant molecules using oxygen and light.

2. The method of claim 1 wherein said core material is selected from the group consisting of amine coated polymeric beads, amine coated glass beads, amine functional dendrimer coated polymeric beads, amine-functional dendrimer coated glass beads and amine functional multigenerational dendrimers.

3. The method of claim 2 wherein said outer portion comprises a polyelectrolyte film bonded to said condensed carbon molecules via amine groups.

4. The method of claim 3 wherein said polyelectrolyte film is selected from the group consisting of layered polyelectrolyte films and hyperbranched polymer films.

5. The method of claim 4 wherein said layered polyelectrolyte films comprise alternating layers of polyanions and polycations.

6. The method of claim 5 wherein said polycations are selected from the group consisting of poly(ammoniums), poly(sulfoniums), and poly(phosphoniums) and said polyanions are selected from the group consisting of poly(acrylates), poly(aspartates), poly(sulfonates), poly(phosphates) and poly(phenoxides).

7. The method of claim 4 wherein said hyperbranched polymer films comprise amino terminated poly(tert-butyl acrylate) bonded to polyelectrolyte films.

8. The method of claim 7 wherein said poly(tert-butyl acrylate) groups include additional acid groups.

9. The method of claim 8 wherein said additional acid groups are activated by ethyl chloroformate.

10. The method of claim 9, wherein cyclodextrins having chiral pockets are bonded to said ethyl chloroformate activated acid groups.

11. The method of claim 3, wherein cyclodextrins having chiral pockets are bonded to said polyelectrolyte film.

* * * * *